US007030290B2

(12) United States Patent
Verwaerde et al.

(10) Patent No.: US 7,030,290 B2
(45) Date of Patent: *Apr. 18, 2006

(54) ***CAENORHABDITIS ELEGANS* STRAIN HD8: A MUTANT EXHIBITING CONSTITUTIVE PHARYNGEAL PUMPING**

(75) Inventors: Philippe Verwaerde, Neuville en Ferrain (FR); Richard Feichtinger, Ghent (BE); Myriam Behgyn, Ghent (BE); Thierry Bogaert, Kortrijk (BE)

(73) Assignee: Devgen NV, Ghent-Zwijnaarde (BE)

( * ) Notice: Subject to any disclaimer, the term of this patent is extended or adjusted under 35 U.S.C. 154(b) by 239 days.

This patent is subject to a terminal disclaimer.

(21) Appl. No.: 10/638,670

(22) Filed: Aug. 11, 2003

(65) Prior Publication Data

US 2004/0034880 A1 Feb. 19, 2004

Related U.S. Application Data

(63) Continuation of application No. 09/549,411, filed on Apr. 14, 2000, now Pat. No. 6,664,441.

(30) Foreign Application Priority Data

Apr. 15, 1999 (GB) ................................. 9908677.9

(51) Int. Cl.
*A01K 67/00* (2006.01)
*A01K 67/33* (2006.01)
(52) U.S. Cl. .............................................. 800/8; 800/3
(58) Field of Classification Search ..................... 800/8
See application file for complete search history.

(56) References Cited

U.S. PATENT DOCUMENTS 6,664,441 B1 * 12/2003 Verwaerde et al. ............ 800/3

FOREIGN PATENT DOCUMENTS

WO WO 01/40500 A1 6/2001

OTHER PUBLICATIONS

B.Y. Tsai et al., "Artificial Feeding Systems for Plant-Parasitic Nematodes," Journal of Nematology, vol. 22, No. 3, (1990), pp. 327-332.
RJ Wall, Theriogenology, "Transgenic Livestock: Progess and Prospects for the Futture," 1996, 45:57-68.
L-M Houdebine, Journal of Biotechnology, "Production of pharmaceutical proteins from transgenic animals," 1994, 34: 269-287.
KM Ebert et al., Molecular Endocrinology, "A Moloney MLV-Rat Somatotropin Fusion Gene Produces Biologically Active Somatotropin in a Transgenic Pig," 1988, 2:277-283.
CA Kappel et al, Current Opinion in Biotechnology, "Regulating gene expression in transgenic animals," 1992, 3:548-553.
LJ Mullins et al., J. Clin. Invest., "Perspectives Series: Molecular Medicine in Genetically Engineered Animals," 1996, vol. 98 No. 11, pp. S37-S40.
RE Hammer et al., J. Anim. Sci., "Genetic Engineering of Mammalian Embryos," 1986, 63:269-378.
RM Strojek et al., Genetic Engineering: Principles and methods, Plenum Press, 1988, vol. 10, pp. 221-246.

* cited by examiner

*Primary Examiner*—Scott D. Priebe
(74) *Attorney, Agent, or Firm*—Wolf, Greenfield & Sacks, P.C.

(57) ABSTRACT

The invention provides methods of screening compounds for potential pharmacological activity using nematode worms, principally but not exclusively the nematode *C. elegans*. Specifically, the invention relates to the use of nematodes modified to have certain characteristics which provide advantages for compound screening, such as constitutive pharyngeal pumping, increased gut permeability or altered gut molecular transport. Methods for selecting suitably modified nematodes from a population of nematodes are also provided.

2 Claims, 4 Drawing Sheets

FIG. 1. GUT LUMEN STAINING

STAINING OF THE GUT CELLS, NOT THE GUT LUMEN.

INCREASED DRUG SENSITIVITY OF GUN MUTATIONS.

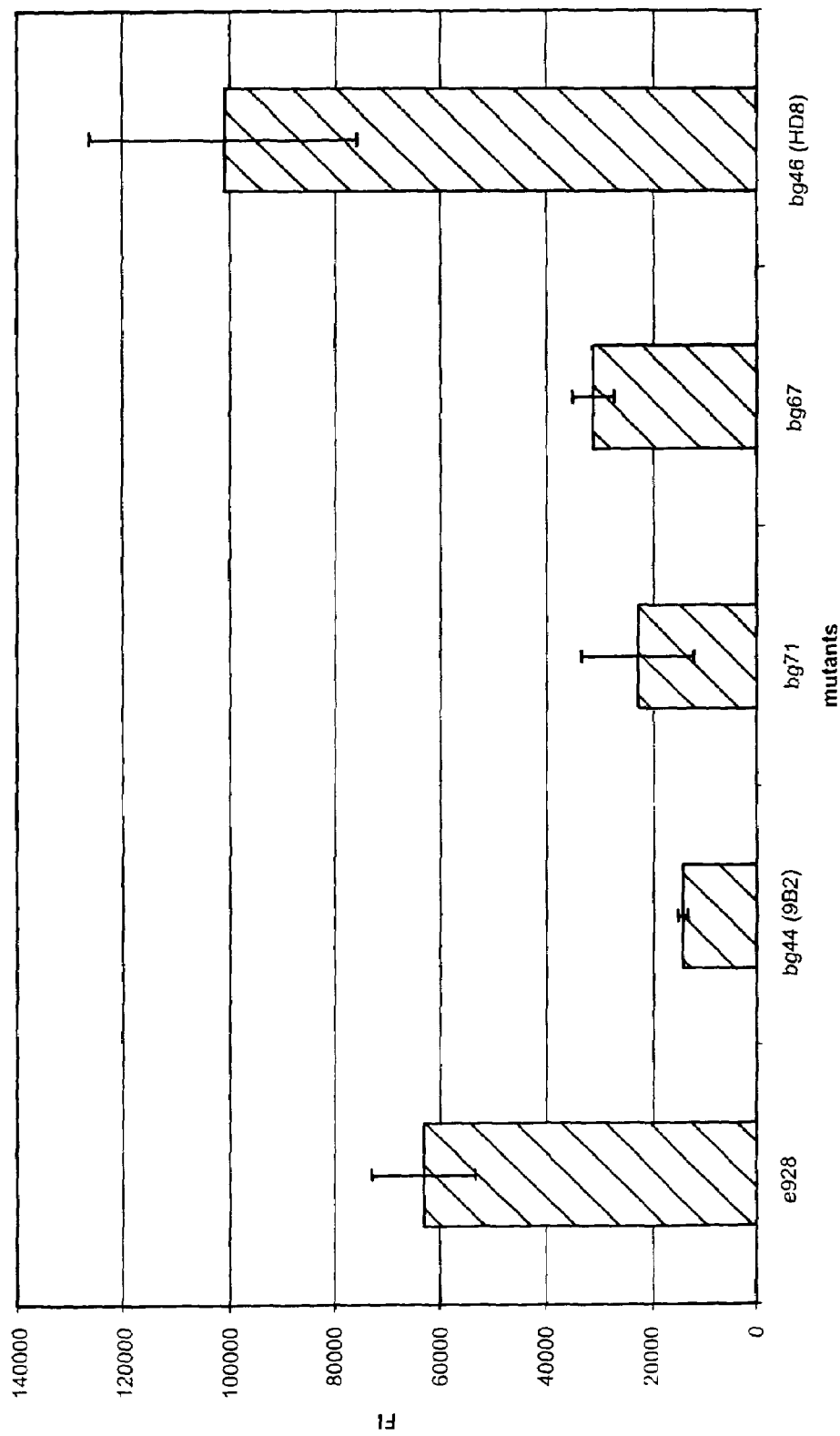
FIG. 4. DRINKING ASSAYS: HIGH DRINKERS

CAENORHABDITIS ELEGANS STRAIN HD8: A MUTANT EXHIBITING CONSTITUTIVE PHARYNGEAL PUMPING

RELATED APPLICATIONS

This application claims the benefit under 35 U.S.C. § 120 of U.S. application Ser. No. 09/549,411, entitled "Compound Assay," filed on Apr. 14, 2000 now U.S. Pat. No. 6,664,441, which is herein incorporated by reference in its entirety.

BACKGROUND OF THE INVENTION

The invention relates to the field of genetic pharmacology and in particular to the screening of compounds for potential therapeutic activity using nematodes, principally but not exclusively, the nematode *Caenorhabditis elegans*. Specifically, the invention relates to the use of nematodes modified to have characteristics suitable for compound screening and to methods of selecting suitably modified nematodes from a population of nematodes. *Caenorhabditis elegans* is a nematode worm which occurs naturally in the soil but can be grown easily in the laboratory on nutrient agar or in liquid nutrient broth inoculated with bacteria, preferably *E. coli*, on which it feeds. Each worm grows from an embryo to an adult worm of about 1 mm long in three days or so. As it is fully transparent at all stages in its life, cell divisions, migrations and differentiation can be seen in live animals. Furthermore, although its anatomy is simple its somatic cells represent most major differentiated tissue types including muscles, neurons, intestine and epidermis. Accordingly, differences in phenotype which represent a departure from that of a wild-type worm are relatively easily observed, either directly by microscopy or by using selective staining procedures. Many *C. elegans* mutants have been identified and their phenotype described, for example see *C. elegans* II Ed. Riddle, Blumenthal, Meyer and Priess, Cold Spring Harbor Laboratory Press, 1997. Furthermore, standard methods are known for creating mutant worms with mutations in selected *C. elegans* genes, for example see J. Sutton and J. Hodgkin in "The Nematode *Caenorhabditis elegans*", Ed. by William B. Wood and the Community of *C. elegans* Researchers CSHL, 1988 594–595; Zwaal et al, "Target-Selected Gene Inactivation in *Caenorhabditis elegans* by using a Frozen Transposon Insertion Mutant Bank" 1993, Proc. Natl. Acad. Sci. USA 90 pp 7431–7435; Fire et al, Potent and Specific Genetic Interference by Double-Stranded RNA in *C. elegans* 1998, Nature 391, 860–811.

The *C. elegans* genome is now entirely sequenced and is available in a public database of the Wellcome Trust Sanger Institute. As a result of the *C. elegans* genome sequencing project, it has emerged that *C. elegans* comprises genes which have equivalents that are widely distributed in most or all animals including humans.

The possibility that *C. elegans* might be useful for establishing interactions between external molecules and specific genes by comparison of *C. elegans* phenotypes which are generated by exposure to particular compounds and by selected mutations is considered by Rand and Johnson in Methods of Cell Biology, Chapter 8, volume 84, *Caenorhabditis elegans*: Modern Biological analysis of an Organism Ed. Epstein and Shakes, Academic Press, 1995 and J. Ahringer in Curr. Op. in Gen. and Dev. 7, 1997, 410–415.

Rand and Johnson in particular describe compound screening assays in which varying concentrations of the compound to be tested are added to nutrient agar or broth which is subsequently seeded with bacteria and then inoculated with worms. Any phenotypic changes in the worm as a result of exposure to the compound are then observed.

Although the nematode and in particular, *C. elegans*, is proving a powerful and efficient tool in the identification or discovery of pharmacologically active molecules, the presently known techniques for compound screening are not without drawbacks. A particular problem is that *C. elegans*, like higher organisms, is endowed with physiological barriers which prevent or minimise the ingress of foreign and potentially harmful substances. Because it normally lives in the dirt, this nematode has evolved a high number of pgp and mdr genes (Table 2) and hence has a high detoxification capacity which is a disadvantages for laboratory drug discovery purposes. In the past the only way in which these barriers have been overcome is to expose the worm to a high concentration of the compound to be tested, for example in the millimolar range. This is inconvenient because many of the compounds which might be screened in *C. elegans* are either only available in micromolar quantities or it is not economically feasible to use concentrations any higher than this. Furthermore, high concentrations of compounds may lead to death of the bacteria and hence starvation of the nematodes. It has also been observed that compounds crystallize when applied in high concentration.

If a compound is to reach a particular target in *C. elegans* it must overcome barriers in the pharynx, and in the gut and/or the cuticle. *C. elegans* feeds by taking in liquid containing its food (e.g. bacteria). It then spits out the liquid, crushes the food particles and internalises them into the gut lumen. This process is performed by the muscles of the pharynx. The process of taking up liquid and subsequently spitting it out is called pharyngeal pumping. Since this pumping process is stimulated to take place mainly in the presence of food, the pharynx is not pumping all the time in wild-type *C. elegans*. As a result, if worms are placed in a liquid culture in the presence of a dye a slow uptake and large variance in uptake amongst individual worms is observed.

Once a test compound has been internalised then the gut itself is a further frontier that may prevent the test compounds reaching their target site in the worm. This may be due to the presence of modifying and detoxifying enzymes in the gut, examples of which are the multi-drug resistance proteins (P-glycoproteins) and the multi-drug resistance related proteins.

Finally, *C. elegans* possesses a natural barrier to external substances which is the cuticle. The cuticle covers the outermost surfaces of the worm and also lines the pharynx and the rectum. It comprises mainly collagens and is substantially impermeable.

SUMMARY OF THE INVENTION

The present inventors have developed methods for compound screening in which the effect of these barriers to compound uptake is removed or diminished. These methods provide compounds assays of greater sensitivity while reducing the quantity of compound which must usually be used.

Therefore, in accordance with a first aspect of the invention there is provided a method of screening a compound for pharmacological activity which comprises observing a phenotypic change in a nematode when exposed to said compound in which said nematode exhibits constitutive pharyngeal pumping.

By "constitutive pharyngeal pumping" is meant constant pumping irrespective of the external or internal stimuli which would normally induce or repress such pumping.

The nematode may exhibit constitutive pharyngeal pumping as a result of a mutation in a relevant gene or alternatively may comprise a transgene which facilitates this phenotypic effect. Furthermore, the nematode may have other mutations or transgenes which result in the manifestation of another phenotypic characteristic which could be effected by the compound to be tested.

Caenorhabditis elegans is the most preferred nematode worm for use in the method of the invention. However, it will be appreciated that the method may also be carried out with other nematodes and in particular with other microscopic nematodes, preferably microscopic nematodes belonging to the genus Caenorhabditis. As used herein the term "microscopic" nematode encompasses nematodes of approximately the same size as C. elegans, being of the order 1 mm long in the adult stage. Microscopic nematodes of this approximate size are extremely suited for use in mid- to high-throughput screening as they can easily be grown in the wells of a multi-well plate of the type generally used in the art to perform such screening.

As aforesaid pharyngeal pumping is facilitated in C. elegans by the pharynx muscles and the contraction of these muscles is controlled by a set of neurons. A list of the thirty-seven neurons and/or structural cells associated with the pharynx and pharyngeal pumping is shown in Table 4. A worm which exhibits an altered function in one or more of these neurons or cells which results in constitutive pharyngeal pumping is preferred for use in the method of the invention. In particular embodiments of the method, use of a worm exhibiting an altered function in one or more of the neurons, which according to C. elegans nomenclature are called MC, M3, M4 and NSM is preferred. These cells have been shown to control, respectively, the rate of pumping, timing of muscle relaxation, isthmus peristalsis and perception of food.

The main neurotransmitters involved in pharyngeal signalling have been identified as acetylcholine and serotonin, which are respectively functional in MC and NSM neurons. Other neurotransmitters such as glutamate, octopamine, dopamine, γ-aminobutyrate (GABA) and FMRF have also been shown to play a role in pumping. Accordingly, any mutant or transgenic worm which exhibits altered levels of one or more of these neurotransmitters may be suitable for use in the screening method of the invention. For example increased levels of serotonin are known to increase pharyngeal pumping.

As an alternative to using a worm which exhibits constitutive pharyngeal pumping, compound screening assays can be carried out in which a worm, wild-type in respect of pharyngeal pumping, is exposed both to the compound to be tested and a compound which induces or increases pharyngeal pumping. Such a compound for inducing or increasing pharyngeal pumping may be one of the neurotransmitters listed above or an agonist or antagonist of any one of these neurotransmitters, for example a serotonin agonist.

The benefit of using a worm in a compound screening assay which exhibits constitutive pharyngeal pumping, or has additional pharyngeal pumping induced, is that the worm will take up more medium into the gut as a function of time, independently of the presence of food in the medium. Furthermore, more of the compound which is dissolved in the medium will pass into the lumen of the gut. Thus, a higher concentration is available at that site to negotiate the gut barrier as discussed below. An additional advantage is that C. elegans populations with a constantly pumping pharynx grow more synchronously in the medium as their food uptake is more regular. This has the effect of simplifying the phenotypic observations which need to be made in a compound screen.

In accordance with a second aspect of the invention there is provided a method of screening a compound for potential pharmacological activity which comprises observing a phenotypic change in a nematode on exposure to said compound wherein said nematode exhibits increased gut permeability or increased uptake of foreign molecules through the gut wall. The nematode is preferably a microscopic nematode, as defined above, more preferably Caenorhabditis sp and may be a mutant or a transgenic worm comprising one or more mutations or transgenes which increase gut permeability or uptake and may also be responsible for the manifestation of another phenotypic characteristic associated with the target of the compound to be tested.

There are multiple factors which effect the uptake of compounds from the gut lumen to the surrounding tissues. These include the action of multi-drug resistance proteins (the P-glycoproteins) and the multi-drug resistance related proteins (MRPs) as well as other enzymes and mechanisms available for transport of molecules through the gut wall. Since test compounds will only reach the lumen of the gut through the pharynx it is preferable if worms which exhibit increased gut permeability or increased gut transport of foreign molecules also show constitutive pharyngeal pumping so that increased amounts of the test compound are both introduced into the gut lumen and transported into the surrounding tissues.

As an alternative to using a worm which exhibits increased gut permeability or increased gut transport of foreign molecules, compound screening assays may be performed in which a worm, wild-type in respect to gut permeability and uptake, is exposed to the compound to be tested and a compound which induces or increases the gut permeability or gut uptake. Such a compound may be a compound which inhibits or decreases the activity of multi-drug resistance proteins or multi-drug resistance related proteins or detoxification proteins. An example of these is cyclosporin A which inhibits the activity of multi-drug resistance proteins.

Worms, in particular microscopic nematodes such as C. elegans, which have been modified to increase the permeability of the outer cuticle are also useful for compound screening assays. Increased cuticle permeability may be a feature manifested in worms which also show constitutive pharyngeal pumping and increased gut permeability or increased gut uptake of foreign molecules. Worms with increased cuticle permeability may be transgenic or mutant worms obtained or created as aforesaid or alternatively they can be generated by treating the outer cuticle of the worms with a substance which induces cuticle permeability such as collagenase or bleach.

In one embodiment assays may be performed in which a wild-type worm is exposed to the compound to be tested and an enzyme or other suitable compound which creates or induces cuticle permeability.

It will be appreciated that worms having modifications such as those described above have significant advantages in compound screening assays since they are able to take up more compound, thereby increasing the sensitivity of the assay while reducing the amount of compound which must be used and hence the cost.

By "compound" is meant herein is any foreign molecule not usually present in the worm or to which the worm would not normally be exposed during its life cycle. For example, the worm may be exposed to a compound listed in a pharmacopoeia with known pharmacological activity. Alternatively, the compound may be one known to interact with a particular biochemical pathway or gene. A further alternative is to test known molecules with no known biological activity or completely new molecules or libraries of molecules such as might be generated by combinatorial chemistry. Compounds which are DNA, RNA, PNA, polypeptides or proteins are not excluded. Altered worm phenotypes which occur as a result of the compound exposure may be detected using light microscopy, differential interference contrast optics or fluorescence microscopy. In addition immuno-chemical detection, calorimetric detection or detection of fluorescence, luminescence or radioactive labels may be used. In some cases changed characteristics may be biochemical only and might be detected, for example by a change in pH in the growth media or a change in electrical potential. Different characteristics may need to be determined at different points in the growth cycle of the worm.

C. elegans mutants with the appropriate characteristics for increased compound intake as described above may be obtained from the C. elegans mutant collection at the C. elegans Genetic Center, University of Minnesota, St Paul, Minn., but may also be generated by standard methods. Such methods are described by Anderson in Methods in Cell Biology, Vol 48, "C. elegans: Modern biological analysis of an organism" Pages 31 to 58. Several selection rounds of the PCR technique can be performed to select a mutant worm with a deletion in a desired gene. Other methods of generating mutants with targeted defective gene expression are described by Sutton and Hodgkin, Zwaal et al and Fire et al as described above.

As aforesaid, for producing worms with enhanced uptake of compounds through the gut, particular genes which are targets to be mutated, deleted or otherwise knocked out are genes encoding multi-drug resistance proteins and multi-drug resistance related proteins.

In respect of generating mutant worms exhibiting constitutive pharyngeal pumping a target gene for modification is one encoding a protein involved in a pathway associated with the processing of one or more of the neurotransmitters acetylcholine, serotonin, glutamate, octopamine, dopamine, GABA or FMRF with a view to altering the levels thereof.

By "processing" is meant synthesis, transport, storage, release, re-uptake or degradation of the listed neurotransmitter.

As an alternative to mutation, transgenic worms may be generated with the appropriate characteristics. Methods of preparing transgenic worms are well known in the art and are particularly described by Craig Mello and Andrew Fire, Methods in Cell Biology, Vol 48, Ed. H. F. Epsein and D. C. Shakes, Academic Press, pages 452–480.

Following interventions to the worm to generate the relevant modifications to increase compound uptake as described above, it is necessary to be able to identify easily worms with the desired features and in particular those which exhibit the desired characteristics most strongly. Methods are available in the art for identification of mutant worms, such as those already listed. Alternatively, a genetic analysis may be used. However, a method which is specific for detecting worms with increased compound uptake is particularly desirable.

The present inventors have now developed a quicker and much more sensitive method to detect modified worms demonstrating the required degree of pharyngeal pumping and increased gut or cuticle permeability or compound uptake.

Thus, in accordance with a third aspect of the invention there is provided a method of identifying a mutant or transgenic nematode exhibiting increased uptake of compounds to be tested for potential pharmacological activity through the pharynx and/or gut and/or cuticle which comprises exposing said nematode to a compound incorporating a marker molecule which provides a detectable signal when taken up by the nematode and comparing the strength of said signal with the signal obtained from a wild-type worm when exposed to said marker molecule.

Preferably, the compound incorporating the marker molecule is one which only gives off its detectable signal once internalised in the worm, for example when cleaved by a worm enzyme or exposed to an environment found solely inside the worm.

In a particular embodiment the inventors have found that the fluorescent dye precursor calcein-AM available from Molecular Probes Europe BV, The Netherlands, is taken up through the pharynx by the worm and subsequently fluoresces, after cleavage of the AM moiety, in the gut lumen and/or in the surrounding cells if it passes the gut barrier. Worms which are able to take up more of the dye because of increased pharyngeal pumping fluoresce very brightly amongst a population of worms without that characteristic and therefore can be easily identified. Furthermore, the level of fluorescence can be quantified by methods known to those skilled in the art, thereby identifying those worms with the highest levels of pharyngeal pumping.

Because calcein fluoresces so brightly it is difficult to tell whether all of the fluorescent material remains in the gut lumen or whether any of it has passed to the surrounding cells and hence through the gut wall. In another embodiment the inventors have used a different fluorescent probe, BCECF-AM available from Molecular Probes (Europe BV), Netherlands. This dye only becomes fluorescent when cleaved by esterases and maintained at a pH above 6. The pH of the gut lumen is usually 5 or below. Thus, any BCECF-AM taken up through the pharynx into the gut lumen is not fluorescent until cleaved and the cleaved portion has entered the cells surrounding the lumen which are at a higher pH. Thus, this dye is able to quickly identify those mutants or otherwise modified worms which have increased gut transport or permeability. There is a gradual increase in fluorescence in the tissues surrounding the gut while the gut lumen remains dark. The fluorescence can be detected at an excitation wavelength of 485 nm and an emission wavelength of 530 nm.

Other compounds incorporating marker or signal generating molecules which will give a fluorescent signal include fluorescein diphosphate (FDP) and CMB-leu which are substrates of alkaline phosphate and endoproteases respectively.

As an alternative the marker molecule may be luminescent such as AMPPD or a glucorondiase substrate giving a coloured signal such as 5-bromo-4-chloro-3-indolyl glucuronic acid (X-gluc). All these compounds incorporating marker molecules may be obtained from molecular Probes Europe BV, The Netherlands.

A method of isolating mutant C. elegans strains which exhibit increased gut uptake (designated herein as gun mutant strains) using the marker dye BCECF-AM is described in the accompanying Examples. A specific gun mutant strain isolated using this procedure, strain bg85, was deposited on 23 Dec. 1999 in accordance with the provisions of the Budapest Treaty on the International Recognition of the Deposit of Microorganisms in the Belgian Coordinated Collections of Microorganisms-BCCM LMBP-Collection, Universiteit Gent, K. L. Ledeganckstraat 35, B-9000, Gent, Belgium under accession number LMBP 5334CB.

A *C. elegans* strain which exhibits constitutive pharyngeal pumping, designated strain HD8 or bg46 or hdr(bg46) see Example 1 below, was deposited on 9 Feb. 2000 in accordance with the provisions of the Budapest Treaty on the International Recognition of the Deposit of Microorganisms in the Belgian Coordinated Collections of Microorganisms-BCCM LMBP-Collection, Universiteit Gent, K. L. Ledeganckstraat 35, B-9000, Gent, Belgium under accession number LMBP 5447CB.

In accordance with a fourth aspect of the invention there is provided a method of generating a *C. elegans* mutant exhibiting increased compound uptake which comprises:
(a) providing a mutant nematode with a defect in a gene expressing an enzyme in an anabolic pathway resulting in a characterizable phenotype,
(b) culturing said mutant in medium comprising a compound which is capable of rescuing the phenotype at a concentration which is insufficient to rescue the mutant phenotype,
(c) applying mutagenesis to a population of said mutants, and
(d) selecting those mutants which are restored to a substantially wild-type phenotype.

Further characterization using the uptake assays described herein may be used to distinguish whether the increase of sensitivity is a general property due to increased compound uptake or is specific to the neurotransmitter in question.

In a particular embodiment the inventors have used the *C. elegans* mutant cha-1(cn101ts), which has a mutation in the gene encoding the choline acetyltransferase. A temperature sensitive mutation displays slow pumping, impaired movement and grows slowly. The effect can be rescued by exposing the worms to acetylcholine in the medium. This mutant can be grown on sub-rescuing amounts of acetylcholine, i.e. at a concentration that is only slightly lower than the rescuing concentration. Any additional mutation, induced by conventional mutagenesis as is state of the art, may increase the sensitivity of the cha-1 mutation to the acetylcholine that is in the medium in low concentration and thereby increase the growth rate considerably. In that way mutant worms sensitive to the neurotransmitter can be selected. In a final aspect, the invention further provides for use of *C. elegans* strains with enhanced pharyngeal pumping, and/or enhanced gut uptake, and/or decreased drug metabolism, as described herein, in toxicity screening. In particular, the invention provides methods of testing compounds for potential toxicity which comprise observing a phenotypic change in a nematode when exposed to said compound wherein the nematode exhibits enhanced or constitutive pharyngeal pumping, increased gut permeability or gut molecular transport or increased cuticle permeability.

Worms with increased permeability (i.e. defects in cuticle or gut barrier), increased pharynx pumping activity, or decreased ability to metabolise or to remove xenobiotics from the intracellular compartment into the gut lumen, relative to wild-type worms, would display a greater sensitivity to toxic compounds in general. Such worms designated as "sensitised" worms could be used to screen compounds for toxicity.

For the avoidance of doubt, where particular characteristics or properties of nematode worms are described herein by relative terms such as "enhanced" or "increased" or "decreased" this should be taken to mean enhanced, increased or decreased relative to wild-type nematodes. In the case of *C. elegans* wild-type is defined as the N2 stain wich is obtainable from the *C. elegans* Genetic Center, University of Minnesota, St Paul, Minn., USA.

Wild type nematodes in their natural environment live in close contact with xenobiotics synthesised and/or secreted by fungi, bacteria and plants in the soil and for that reason display high ability to prevent a broad range of potentially toxic compounds of diverse chemical structures from entering the internal compartment of the worm body. Thus by a creating a knock-out of these mechanisms of broad protection (structurally speaking), it is possible to open the internal compartment of the worm body (where the molecular targets of the toxin reside) to a wide range of chemical structures.

In the course of the drug discovery process, compounds selected after in vitro pharmacological screening are usually submitted to a wide range of secondary assays. These assays are aimed not only at measuring pharmacokinetic parameters but also at (1) assessing their pharmacological specificity, and (2) verifying the lack of toxicity. These tests are usually in vitro cytotoxicity assays where cell viability is monitored, or more precise measurements of specific mechanisms related to cell viability such as apoptosis, necrosis, DNA synthesis, protein synthesis, free radical production or redox level are made. Sensitised worms may be used as multicellular living models, to test the wide range of active compounds issued from the primary screening for any kind of toxicity, either of metabolic or pharmacological origin. Moreover, the phenotype produced by the toxic compounds could be linked to specific metabolic or pharmacologic pathways, thus giving insights to the mechanism of toxicity.

*Caenorhabditis elegans* is the preferred nematode worm for use in the toxicity testing methods of the invention. However, it will be appreciated that toxicity testing may also be carried out with other nematodes and in particular with other microscopic nematodes, preferably microscopic nematodes belonging to the genus *Caenorhabditis*. As used herein the term "microscopic" nematode encompasses nematodes of approximately the same size as *C. elegans*, being of the order 1 mm long in the adult stage. Microscopic nematodes of this approximate size are extremely suited for use in mid- to high-throughput screening as they can easily be grown in the wells of a multi-well plate of the type generally used in the art to perform such screening.

The nematodes will preferably be mutant or transgenic worms which display the desired characteristics of, for example, enhanced or constitutive pharyngeal pumping, increased gut permeability etc. Specific examples of such mutant and transgenic worms described hereinbefore, e.g. for use in compound screening, are also useful for toxicity testing.

For toxicity testing purposes, the compound under test will preferably be tested at a concentration from 0.1–100 µM. Typically, the compound will be tested at a number of different concentrations within this range, with a preferred range of 1–10 µM.

The read-out or end-point of a toxicity assay may be growth arrest or lethality or it may be a specific phenotype which is associated with exposure of a nematode to a toxic compound. Phenotypes associated with exposure to toxic compounds may be established by exposing the nematode to a compound which has known toxic activity and recording changes in the phenotype of the worm. This phenotype may then be used as the end-point of a toxicity assay.

The invention will now be described with reference to the following figures and examples:

BRIEF DESCRIPTION OF THE DRAWINGS

FIG. 4 illustrates enhanced pharynx pumping in various>drinker=mutant *C. elegans* strains in a standard pharynx pumping assay using calcein-AM. Fluorescence intensity is shown on the Y-axis. To perform the assay 50 worms were added to the wells of 96 well plates in M9 medium, in triplicate, and incubated for 2 h30 with 5 μM of calcein-AM. Fluorescence measurements were made for 1s using calcein standards. Calcein fluorescence may be measured using a standard fluorescence multi-well plate reader with the settings Ex/Em=485/530. Although a wild-type control (N2 strain) is not shown, the values should be interpreted as values above the wild-type.

EXAMPLES

General Methods

Manipulations of *C. elegans* worms may be performed using techniques described in Methods in Cell Biology, vol 84; *Caenorhabditis elegans*: modern biological analysis of an organism, ed. Epstein and Shakes, academic press, 1995, or using minor modifications of the methods described therein.

Example 1

Figure 1:
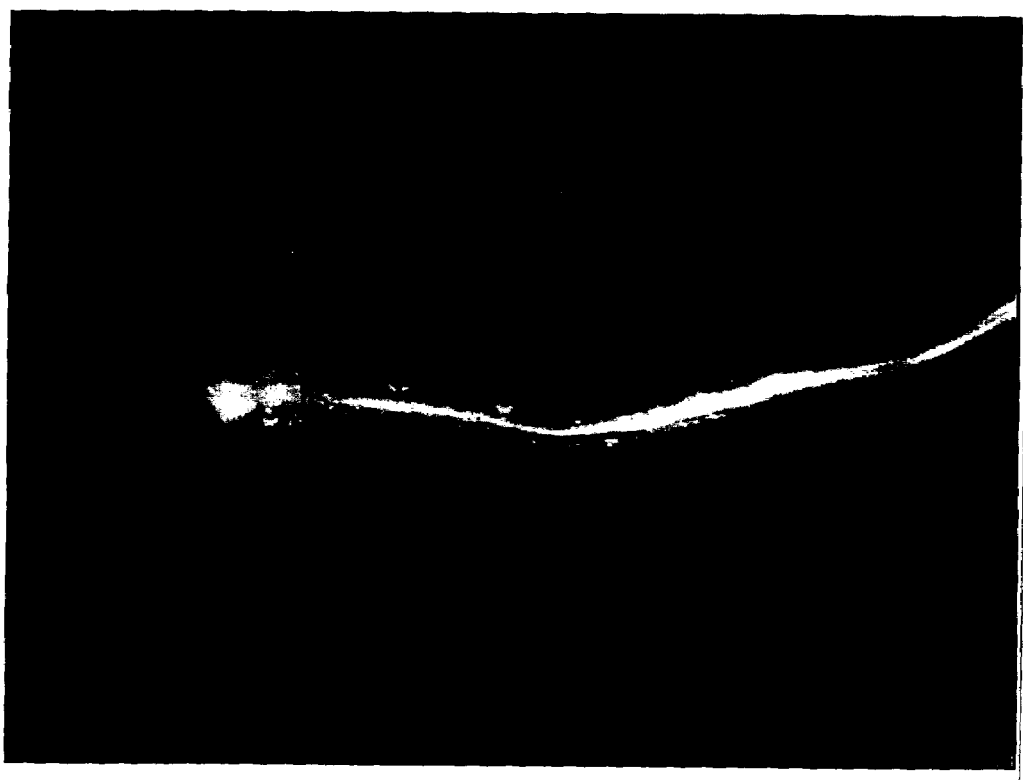
FIG. 1 is a digital representation of a photograph of *C. elegans* showing gut lumen staining with calcein-AM.
Figure 2:
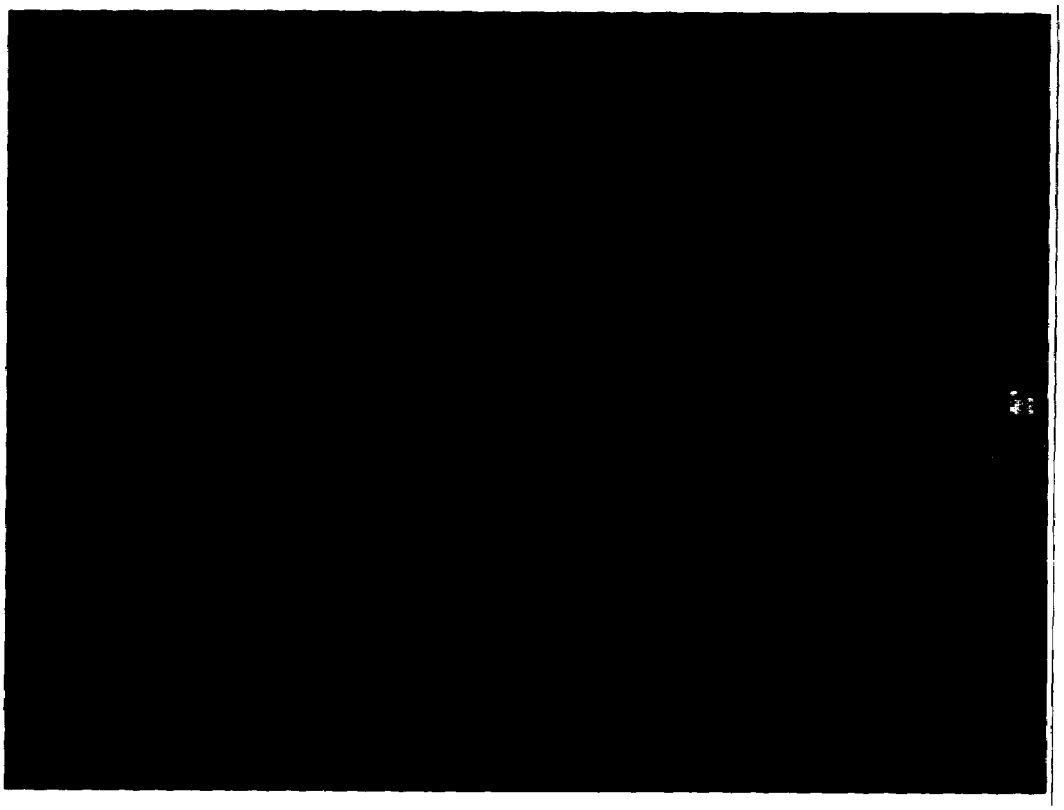
FIG. 2 is a digital representation of a photograph of *C. elegans* showing staining of cells surrounding the gut, and not the lumen, using BCECF-AM.

About 2000 late fourth-larval-stage (L4) *C. elegans* (N2 strain) hermaphrodites were mutagenised by exposure to 50 mM EMS for 4 hours at 20° C. under agitation. Mutagenised worms were then inoculated onto 10 cm nutrient agar plates. Eggs were collected from the F1 progeny and allowed to hatch on the nutrient agar plates. Young F2 adult hermaphrodites were then screened for their ability to stain with calcein-AM. The individuals that were gut stained within 15 minutes were then selected. These worms were mutants with constitutive pharynx pumping and an example is shown in FIG. 1. Those individuals for which the body was also fully stained were shown to have a defective or permeabilized cuticle. The results are shown in Table 1 below.

TABLE 1

| *C. elegans* nematode | Constitutive pharynx pumping | Un-coordinated movement | Other observations | Full staining of body cavity |
|---|---|---|---|---|
| N2 (wild-type) | − | − | − | − |
| Unc-31 (e928) (collection strain) | +++ | ++ | − | − |
| Lon-1 (collection strain) | + | ! | − | −! |
| 9B2 (bg44) | + | − | Eggs, fertility+ | − |
| 3D5 | + | + | − | −/+ |
| HD8 (bg46) | +++ | − | Eggs, fertility− | − |
| 9BR2 | + | − | − | ++ |
| 3D5.FB | + | + | − | ++ |
| Srf-3 (collection strain) | − | − | − | ++ |

Example 2

The genetics of the *C. elegans* gut barrier and detoxification mechanisms.

1. P-glycoproteins

Pgps mediates drug resistance by acting as an ATP-dependent efflux pump removing various lipophilic cytotoxic compounds with the following features (apart from heavy metal specific Pgps):

at least one, preferentially several, planar aromatic ring structures, a cationic charge at physiological pH and a molecular weight around 400 or higher While in humans two Pgp encoding genes are known, of which MDR1 is involved in multi drug resistance, the sequence of *C. elegans* reveals 15 Pgp genes, many of them located in clusters on the X chromosome.

TABLE 2

| Gene | location | expression | mutation | function |
|---|---|---|---|---|
| Pgp-3 | X 3.3 ZK 455.7 F42E11 | apical membrane of intestinal cells and excretory cell | pk18 | Multi drug resistance: deletion mutation increases sensitivity to colchicine 8 fold, chloroquine 3 fold, emetine not increased, ivermectine not increased |
| Pgp-4 | X 3.3 F42E11 | excretory cell | | |
| Pgp-1 | IV 6.0 K08E7 | intestinal cells | pk17 | Heavy metal resistance |
| Pgp-2 | I 0.4 C34G6 | | | |
| Pgp-5 | X 7.6 F22E10 | | | |
| Pgp-6 | X 7.6 F22E10 | | | |
| Pgp-7 | X 7.6 F22E10 | | | |
| Pgp-8 | X 7.6 F22E10 | | | |
| Pgp-9 | II 0.6 DH11 | | | |
| Pgp-10 | X −2 C54D1.1 | | | |
| Pgp-11 | X 2.3 T21E8 | | | |
| Pgp-12 | X 2.3 T21E8 | | | |

TABLE 2-continued

| Gene | location | expression | mutation | function |
|---|---|---|---|---|
| Pgp-13 | X 2.3 T21E8 | | | |
| Pgp-14 | X 2.3 T21E8 | | | |
| Pgp-15 | V 15 C47A10 | | | |

TABLE 3

| Gene | location | expression | mutation | function |
|---|---|---|---|---|
| mrp-1 | X −19.4 F57C12.5 | pharynx, pharyngo-intestinal valve, foregut, vulva, intestine-rectal valve | pk89 | Heavy metal resistance |
| mrp-2 | X F57C12.4 | | | |
| mrp-3 | X 22.4 E03G2 | | | |
| mrp-4 | X 1.23 F21G4 | | | |
| mrp-5 | X 19 F14F4 | | | |
| mrp-6 | X −8 F20B6 | | | |
| mrp-7 | V 21.9 Y43F8 | | | |
| mrp-8 | III 16.2 Y75B8 | | | |

Table 4: Neurons (22) and Structural Cells (15) to be Involved in Controlling Pharyngeal Muscle Function (Pumping)

Pharyngeal Neurons (20, Located in the Pharynx)
  pharyngeal sensory interneurons, I1 gap junctions to extrapharyngeal RIP
I1L, I1R, I2L, I2R, I3, I4, I5, I6
  pharyngeal motor neurons, M3 relaxation control, M4 controls isthmus peristalsis, M3 glutamate as transmitter, others cholinergic
M1, M2L, M2R, M3L, M3R, M4, M5
  pharyngeal motor neurons that synapse to marginal cells, control pumping rate
MCL, MCR
  pharyngeal motor/interneuron
MI
  pharyngeal neurosecretory motor neuron, sense food presence, serotonergic
NSML, NSMR Pharyngeal Structural Cells (15), Electrical Connections)
  Pharyngeal marginal cells (9) that have synaptic input from the MC motor neurons and gap junctions to the pharyngeal muscles. Probably the excitation is electrically conducted to the pharyngeal muscles like the Purkinje fibres in vertebrate hearts.
mc1DL, mc1DR, mc1V, mc2DL, mc2DR, mc2V, mc3DL, mc3DR, mc3V
  pharyngeal sheet cells (6) which form a thin cylindrical sheet between the pharynx and the central nerve ring. Gap junctions with muscle arms and RME body nerve motor neurons, send processes to tip of head.
GLRDL, GLRDR, GLRL, GLRR, GLRVL, GLRVR Neurons (2) that Connect from the Central Nerve Ring to the Pharynx
  gap junctions to I1
RIPL, RIPR legend:
D dorsal
V ventral
L left
R right Example 3

Selecting *C. elegans* mutations for increased gut uptake (gun) using marker dye BCECF-AM and unc-31 as background.

The screen was performed in unc-31(e928) mutant background, to ensure high amounts of dye in the gut lumen, since unc-31 mutations show constitutive pharyngeal pumping. The dye (BCECF-AM: 2',7' bis (2-carboxyethyl)-5-(and-6)-carboxyfluorescein, acetoxymethylester), obtained from Molecular Probes, is cleaved by intracellular esterases. Fluorescence accumulates in the gut cells upon passage through the apical gut membrane.

Mutagenesis
Day 1: unc-31 L4 staged worms were mutagenised with EMS (final concentration 50 mM) for 4 hours
Day 2: P0 was divided over several large agar plates
Day 6: F1's were collected and dropped on large plates. The number of eggs the F1?s layed were checked every hour and de F1?s were removed when 10–20 eggs per F1 were counted
Day 10: F2 adults were collected and screened with BCECF-AM. Mutations with increased staining of the gut cells after 15–30 minutes exposure to the dye were selected and singled on small agar plates.
  About 50 initial positives gave progeny which was retested with BCECF-AM (2×) and leucine CMB (1×)
9 of the 50 strains were kept (2 strains: 3 times positive, 7 other strains : twice positive)

TABLE 5

Isolation of mutations for increased staining with BCECF-AM

| Total P0 (counted) | Total F1 (estimated) | Total F2 (calculated) | screened chromosomes (estimated) | number of strains isolated (counted) |
|---|---|---|---|---|
| 2251 | 55618 | 222472 | 100000 | 9 |

Outcrossing, Backcrossing and Double Construction
1. backcrossing unc-31; gun--> unc-31; gun
  unc-31; gun×WT males
  singled 2×5 WT hermaphrodites F1s (unc-31/+;gun/+)
  singled 50 WT hermaphrodites F2s (¼ homozygous)
  select strains segregating ¼ unc
  stain unc strains with BCECF-AM
  from positive strains pick unc homozygous
  retest 100% unc strains with BCECF-AM kept 1 strain (backcrossed)
2. unc-31 background was crossed out-->+; gun
   unc-31, gun×WT males
   singled 2×5 WT hermaphrodites F1s (unc-31/+;gun/+)
   singled 50 WT hermaphrodites F2s (¼ homozygous)
   select strains which did not segregate unc F3s anymore
   stain non unc strains with BCECF-AM
   7 positive strains were retested with BCECF-AM and finally 1 was selected and kept (outcrossed)
3. +; gun (1× outcrossed) were 2 times backcrossed-->+; gun (3× backcrossed)
   gun×WT males
   WT hermaphrodites×F1 males (gun/+)
   singled 10 WT hermaphrodites F2s (½ heterozygous)
   singled 50 WT hermaphrodites F3s (⅛ homozygous)
   stain strains with BCECF-AM-retested positives with BCECF-AM and finally 1 was selected and kept
4. gun (3× backcrossed) were crossed with nuc-1(X) mutant-->gun; nuc-1
   gun×WT males
   nuc-1×gun/+males
   nuc-1×gun/+; nuc-1/0 or +/+; nuc-1/0 males
   singled 10 WT hermaphrodite progeny (nuc-1 homozygous, ½ heterozygous gun)
   singled 40 WT hermaphrodite progeny (⅛ homozygous gun)
   stain strains with BCECF-AM
   retested positives with BCECF-AM and finally 1 was selected and kept remove supernatant until 2 ml of worm-suspension is left
add 30 L1's per well in a 96 well plate using worm-dispenser apparatus (e.g. the device commercially available from Union Biometrica, Inc, Somerville, Mass., USA which has properties analogous to flow cytometers, such as fluorescence activated cell scanning and sorting devices (FACS))
add S-buffer for a total volume of 100 μl
add chloroquine dilutions in columns (8 replicates for each concentration)
add 1 μl of *E. coli* HB101 (bacterial food source)
incubate plates at 20° C. for 3 days and count number of adults

TABLE 7

Increased drug sensitivity of gun strains

| Strain | genotype | sensitivity increase compared to WT |
|---|---|---|
| NL131 | pgp-3 (pk18) | 3.9 |
| CB928 | unc-31 (e928) | 2.0 |
| UG588 | gun (bg89) | 1.6 |
| UG606 | unc-31; gun (bg89) | 10.3 |
| UG585 | gun (bg87) | 1 |
| UG604 | unc-31; gun (bg87) | 4.5 |

TABLE 6

Strains derived from gun mutations

| gun allele number | unc-31; gun original isolate | | unc-31; gun backcrossed (1x) | | +; gun outcrossed (1x) | | +; gun 3x b.c. | gun; nuc-1 from 3x b.c. |
|---|---|---|---|---|---|---|---|---|
| | isolation number | strain number | isolation number | strain number | isolation number | strain number | strain number | strain number |
| bg77 | 31.4 | UG 510 | 31.4.46.1 | UG 556 | 31.4.34 | UG 563 | UG 674 | UG 777 |
| bg78 | 37.5 | UG 511 | 37.5.46.4 | UG 557 | 37.5.15 | UG 564 | UG 675 | — |
| bg83 | 10.2 | UG 543 | 10.2.11 | UG 600 | 10.2.21 | UG 586 | UG 676 | — |
| bg84 | 7.2 | UG 544 | 7.2.10 | UG 601 | 7.2.15 | UG 589 | UG 677 | UG 774 |
| bg85 | 11.5 | UG 545 | 11.5.29.2 | UG 602 | 2x b.c. | UG 717 | | UG 775 |
| bg86 | 42.1 | UG 546 | 42.1.4.5 | UG 603 | 42.1.18 | UG 587 | UG 678 | UG 776 |
| bg87 | 7.1 | UG 547 | 7.1.8.3 | UG 604 | 7.1.22 | UG 585 | UG 679 | — |
| bg88 | 5.3 | UG 548 | 5.3.9 | UG 605 | 5.3.18 | UG 584 | UG 680 | — |
| bg89 | 23.4 | UG 549 | 23.4.13.5 | UG 606 | 23.4.3 | UG 588 | UG 671 | — |

Drug Sensitivity of Gun Mutants

Aim: Test to see if the gun mutants are more sensitive to drugs than wild type. Chloroquine (C-6628, Sigma) was used as drug and NL131 (pgp-3 knockout) was used as a control (EMBO J. 1995 May 1; 14(9): 1858–66).

Figure 3:
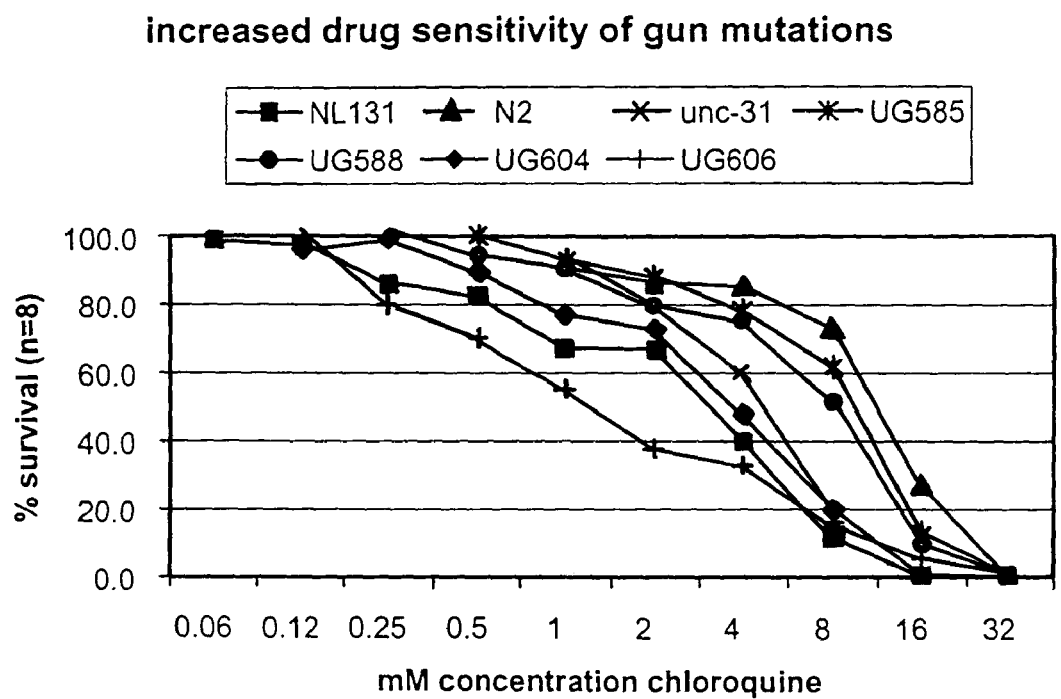
FIG. 3 is a graph to illustrate the increased drug sensitivity of several *C. elegans* gun mutant strains. X-axis is chloroquine concentration (mM), Y-axis is % survival (n=8).

Chloroquine Sensitivity Assay:
chunk stockplates 3 days before L1's are needed
collect worms in S-buffer
centrifuge worm-suspension 1300 rpm 3 min
assemble the filter equipment (use filter of 11 μm)
bring worm-suspension on the filter and rinse a few times with S-buffer.
L1's pass through the filter
centrifuge down the L1 suspension 1300 rpm 3 min FIG. 3 illustrates the increased drug sensitivity of a number of gun mutant strains, as compared to wild-type N2 worms. The gun mutants are generally observed to be more sensitive to the compound chloroquine which is toxic for the worm. This observation indicates that the gun mutants are more sensitive to compounds, which proves the principle of better compound uptake. Because of their increased sensitivity to toxic compounds the gun mutants are useful tools for performing whole organism in vivo toxicity assays.

What is claimed is:
1. A *C. elegans* mutant HD8 (LMBP 5447CB) nematode.
2. A composition comprising *C. elegans* mutant HD8 (LMBP 5447CB) nematodes.

* * * * *